United States Patent
Sokel

(10) Patent No.: US 7,415,861 B2
(45) Date of Patent: Aug. 26, 2008

(54) TISSUE PROSTHESIS PROCESSING TECHNOLOGY

(75) Inventor: Justin Sokel, Flagstaff, AZ (US)

(73) Assignee: Machine Solutions, Inc., Flagstaff, AZ (US)

( * ) Notice: Subject to any disclaimer, the term of this patent is extended or adjusted under 35 U.S.C. 154(b) by 314 days.

(21) Appl. No.: 11/155,119

(22) Filed: Jun. 16, 2005

(65) Prior Publication Data

US 2006/0004469 A1 Jan. 5, 2006

Related U.S. Application Data

(60) Provisional application No. 60/580,244, filed on Jun. 16, 2004.

(51) Int. Cl.
*B21D 39/04* (2006.01)

(52) U.S. Cl. ........................ 72/402; 29/283.5

(58) Field of Classification Search .......... 72/402; 29/237, 282, 283.5
See application file for complete search history.

(56) References Cited

U.S. PATENT DOCUMENTS

| 1,250,113 | A | | 12/1917 | Astrom |
| 1,894,800 | A | * | 1/1933 | Stowe ........................... 72/76 |
| 2,986,192 | A | * | 5/1961 | MacLeod ..................... 29/819 |
| 3,415,105 | A | * | 12/1968 | Brown et al. .................. 72/402 |
| 4,567,650 | A | * | 2/1986 | Balyasny et al. .............. 29/822 |
| 5,411,521 | A | | 5/1995 | Putnam et al. |
| 5,657,656 | A | * | 8/1997 | Evans et al. ................... 72/14.8 |
| 6,082,990 | A | | 7/2000 | Jackson et al. |
| 6,360,577 | B2 | | 3/2002 | Austin |
| 6,568,235 | B1 | | 5/2003 | Kokish |
| 6,651,478 | B1 | | 11/2003 | Kokish |
| 6,823,576 | B2 | | 11/2004 | Austin |
| 6,840,081 | B2 | | 1/2005 | Kokish |
| 6,915,560 | B2 | | 7/2005 | Austin |
| 6,931,899 | B2 | * | 8/2005 | Goff et al. .................... 72/18.1 |
| 7,010,953 | B2 | * | 3/2006 | Stupecky ..................... 72/416 |
| 2002/0138966 | A1 | * | 10/2002 | Motsenbocker .............. 29/516 |

* cited by examiner

*Primary Examiner*—Daniel C Crane
(74) *Attorney, Agent, or Firm*—Skinner and Associates

(57) ABSTRACT

A heart valve prostheses crimping apparatus and method for deducing the diameter of stents containing heart valve prosthesis. A medical prosthesis catheter loading apparatus, including a crimping assembly for reducing the diameter of a prosthesis; and a catheter clamp for holding a catheter adjacent to the prosthesis. Also disclosed is an apparatus for reducing the diameter of a medical prosthesis, including a base, a crimp head connectable to the base, and an actuation mechanism connected to the base and connectable to the crimp head to actuate the crimp head. Also disclosed is a method of loading a medical prosthesis into a catheter, including the steps of reducing the diameter of a prosthesis from its normal deployed state to a diameter less than that of the lumen of the catheter; holding a catheter adjacent to the reduced diameter prosthesis; and moving the prosthesis into the catheter lumen.

14 Claims, 16 Drawing Sheets

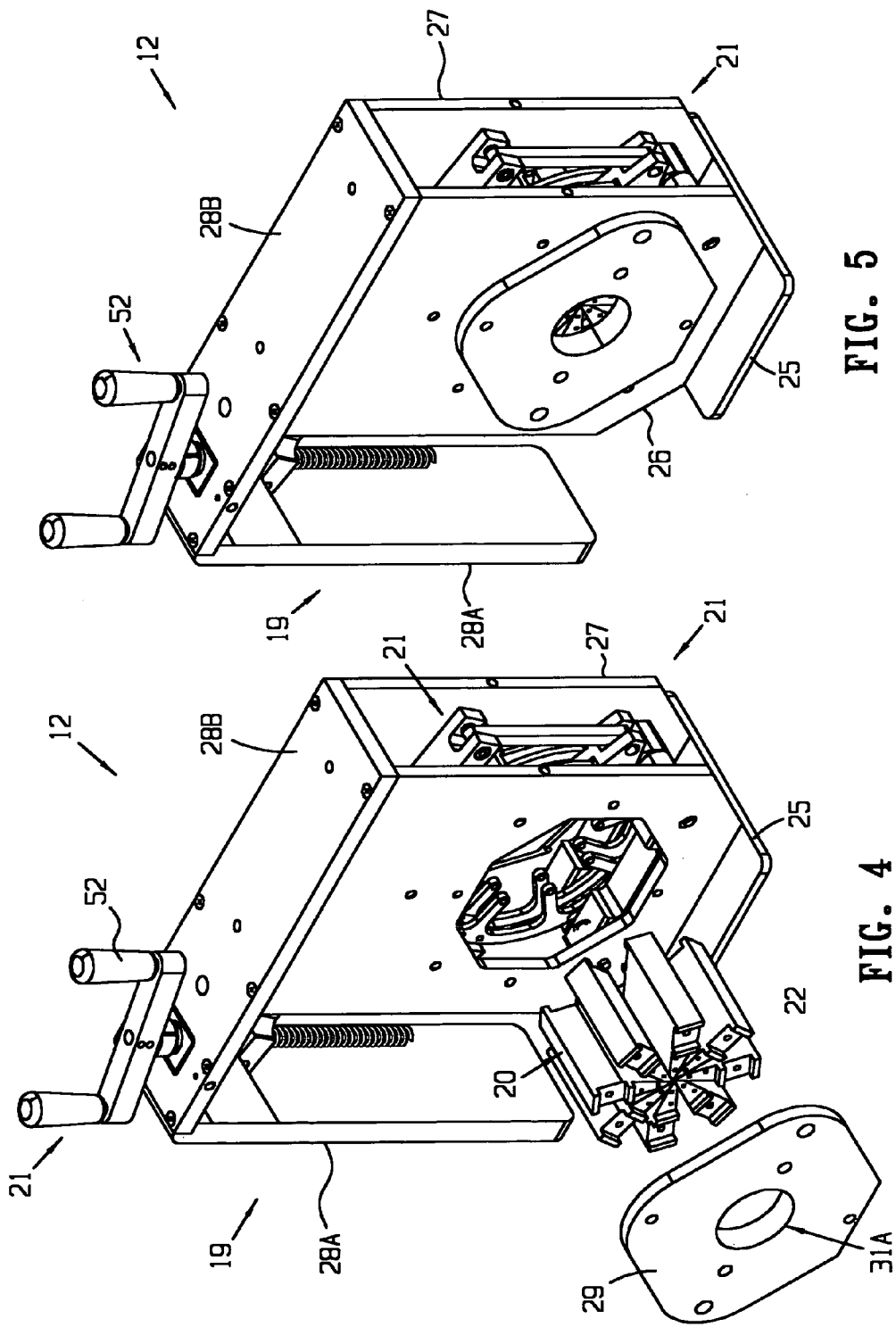

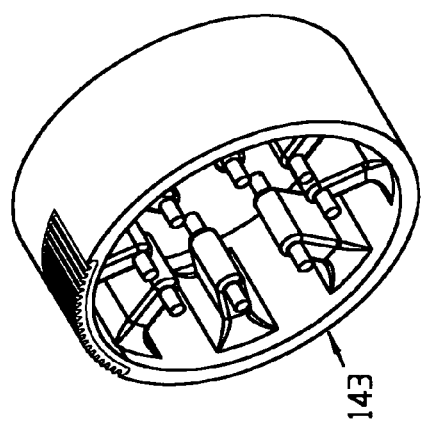
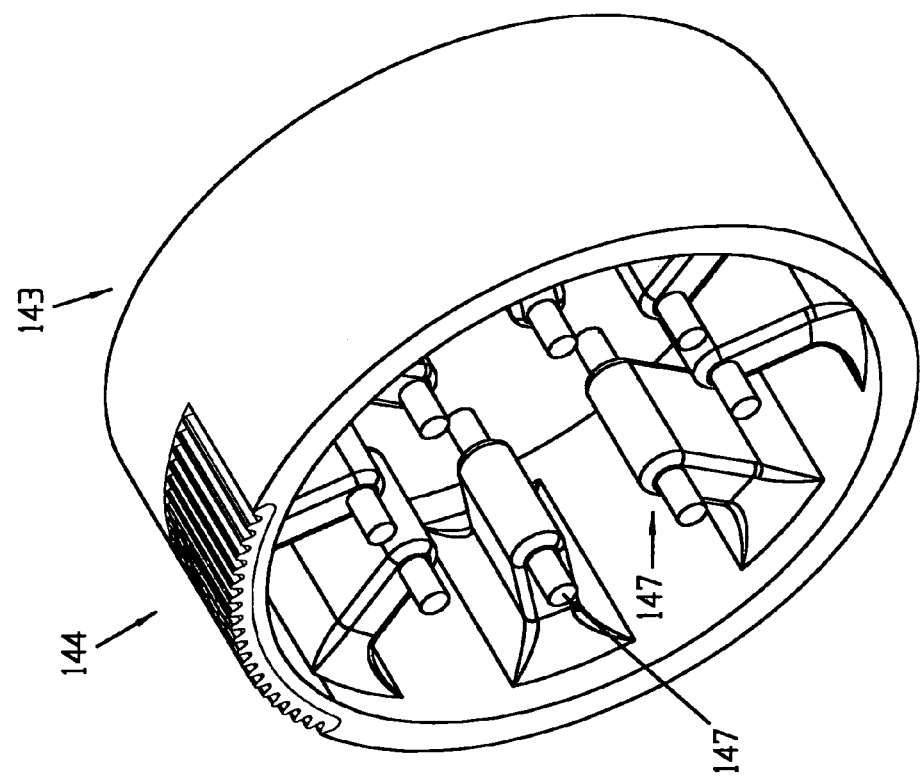

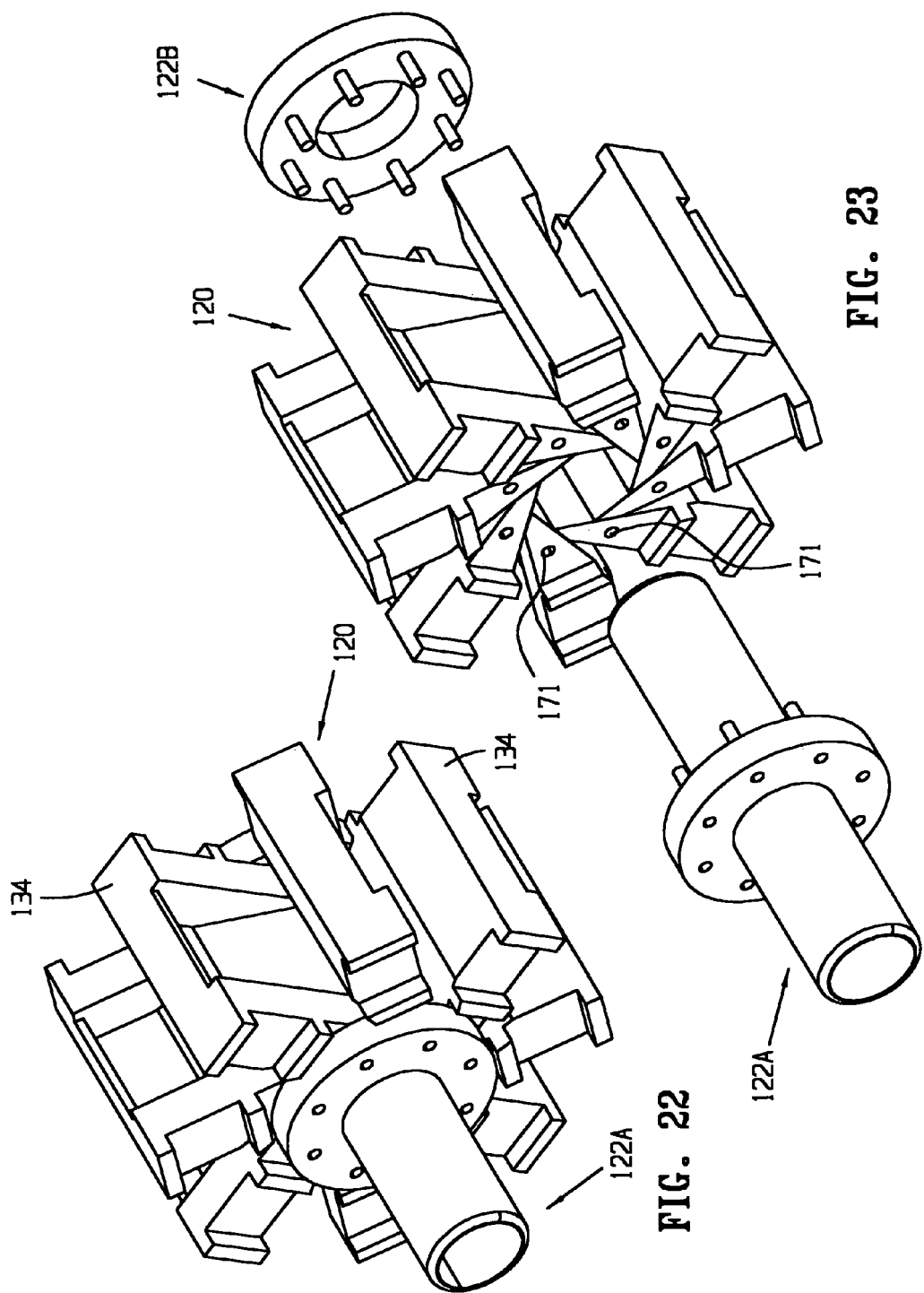

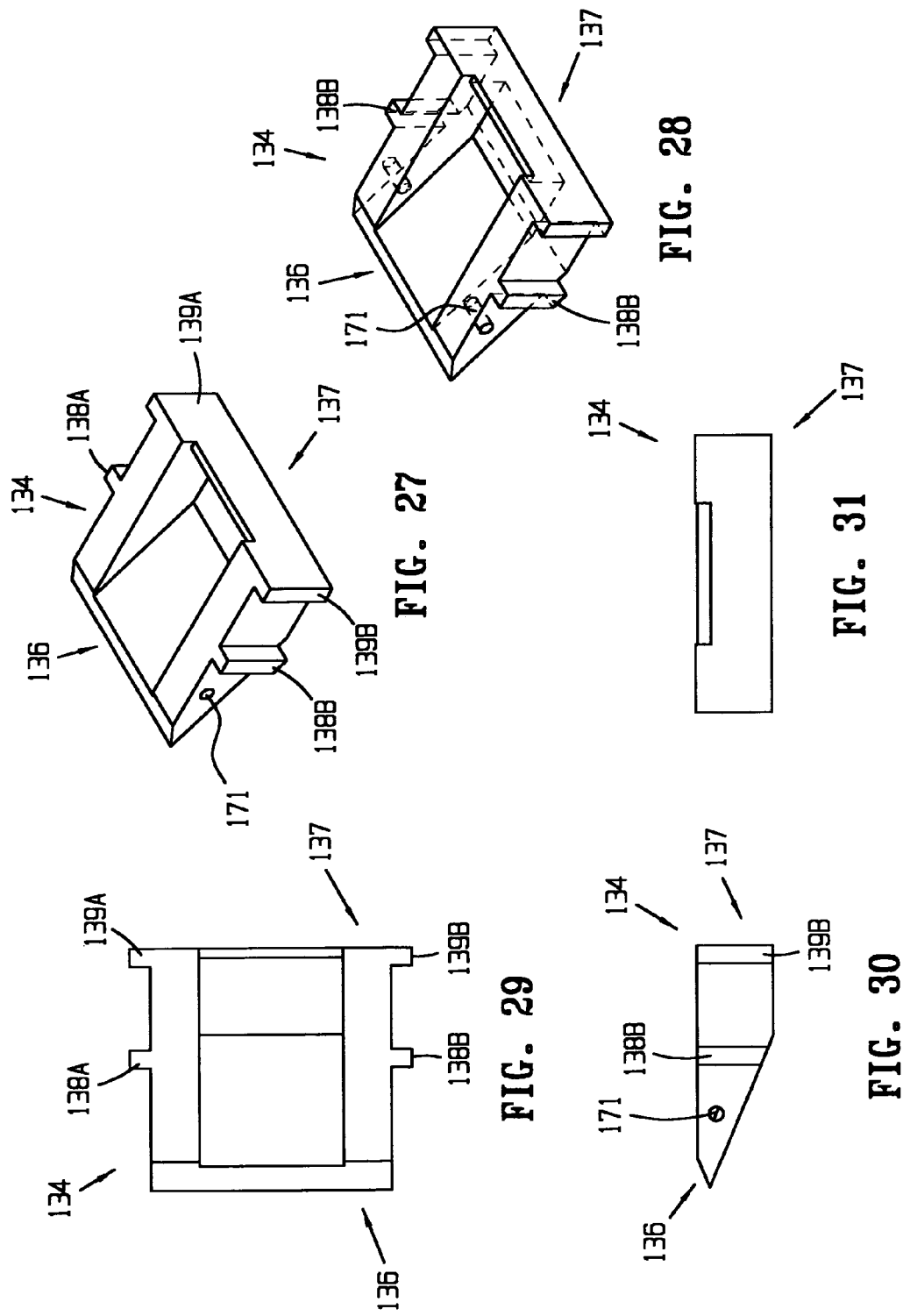

TISSUE PROSTHESIS PROCESSING TECHNOLOGY

CROSS-REFERENCE TO RELATED APPLICATIONS, IF ANY

This application claims the benefit under 35 U.S.C. §119 (e) of co-pending U.S. Provisional Patent Application Ser. No. 60/580,244, filed Jun. 16, 2004, which is/are hereby incorporated by reference.

37 C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND

1. Field

The present invention relates, generally, to medical devices and methods. Particularly, the invention relates to tissue prostheses processing apparatus and methods of making and using tissue prostheses apparatus and systems to process tissue prostheses. More particularly, the invention relates to apparatus and methods for reducing the diameter of tissue prostheses such as heart valves. Most particularly, the invention relates to a heart valve prostheses crimping apparatus and method whereby the diameter of stents containing heart valve prostheses is reduced.

2. Background Information

The state of the art includes stent crimping and balloon folding apparatus and methods produced by applicant's assignee, Machine Solutions, Inc. of Flagstaff, Ariz., USA.

A need is believed to exist for the present invention.

All US patents and patent applications, and all other published documents mentioned anywhere in this application are incorporated by reference in their entirety.

BRIEF SUMMARY

The invention provides a heart valve prostheses crimping apparatus and method which are practical, reliable, accurate and efficient, and which are believed to fulfil the need and to constitute an improvement over the background technology.

In one aspect, the invention provides a medical prosthesis catheter loading apparatus, comprising a crimping assembly for reducing the diameter of a prosthesis; and a catheter clamp for holding a catheter adjacent to the prosthesis.

In another aspect, the invention provides an apparatus for reducing the diameter of a medical prosthesis, comprising a base, a crimp head connectable to the base, and an actuation mechanism connected to the base and connectable to the crimp head to actuate the crimp head.

In a further aspect, the invention provides a method of loading a medical prosthesis into a catheter, comprising the steps of reducing the diameter of a prosthesis from its normal deployed state to a diameter less than that of the lumen of the catheter; holding a catheter adjacent to the reduced diameter prosthesis; and moving the prosthesis into the catheter lumen.

The features, benefits and objects of the invention will become clear to those skilled in the art by reference to the following description, claim(s), if any, and drawings.

BRIEF DESCRIPTION OF THE SEVERAL VIEWS OF THE DRAWING

The present invention, and the manner and process of making and using it, will be better understood by those skilled in the art by reference to the following drawings.

FIG. 4 is an exploded view of the crimping assembly of the apparatus.

FIG. 5 is a perspective view of the crimping assembly.

FIG. 21A-B illustrate an embodiment of the activation ring of the crimping assembly.

FIG. 22 is a perspective view of an embodiment of the disposable crimping head of the crimping assembly, also showing the loader.

FIG. 23 is an exploded view of the crimping head, also showing the loader.

FIG. 27 is a perspective view of an alternative embodiment of a crimping element for use with the crimping head shown in FIGS. 16-25.

FIG. 28 is a view showing the opposite sides in phantom.

FIG. 29 is a view of the lateral side of the segment.

FIG. 30 is a view of the longitudinal side of the segment.

FIG. 31 is a view of the distal end of the segment.

DETAILED DESCRIPTION

The tissue prosthesis crimping apparatus of the present invention is useable by a single operator to easily reduce the diameter of, or crimp, relatively large stents containing tissue prostheses such as heart valves and the like, and loads such device into a catheter for later use and deployment in a patient. It is suitable "bed-side" catheter procedures such as minimally invasive heart valve replacement (MIHVR). The tissue prosthesis crimping apparatus is also useable for bench testing medical devices and product testing such devices with animals.

Figure 1:
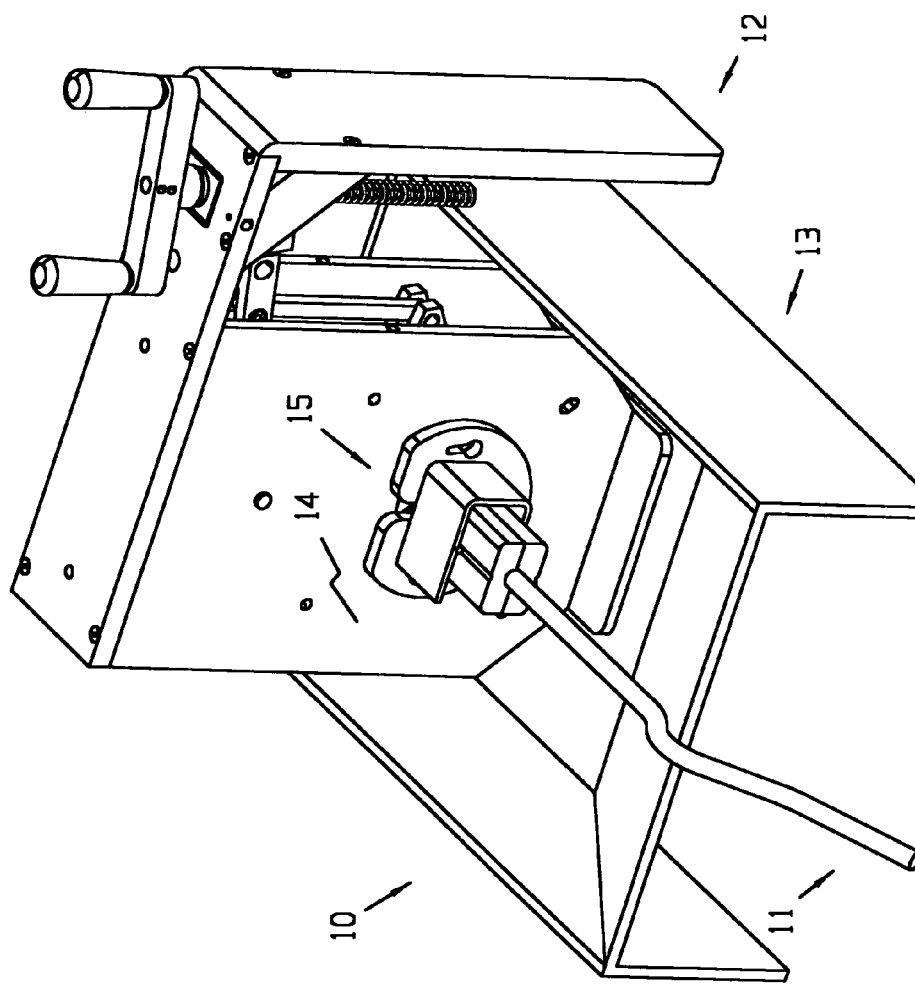
FIG. 1 is a perspective view of one embodiment of the tissue prostheses processing apparatus of the present invention.
Figure 2:
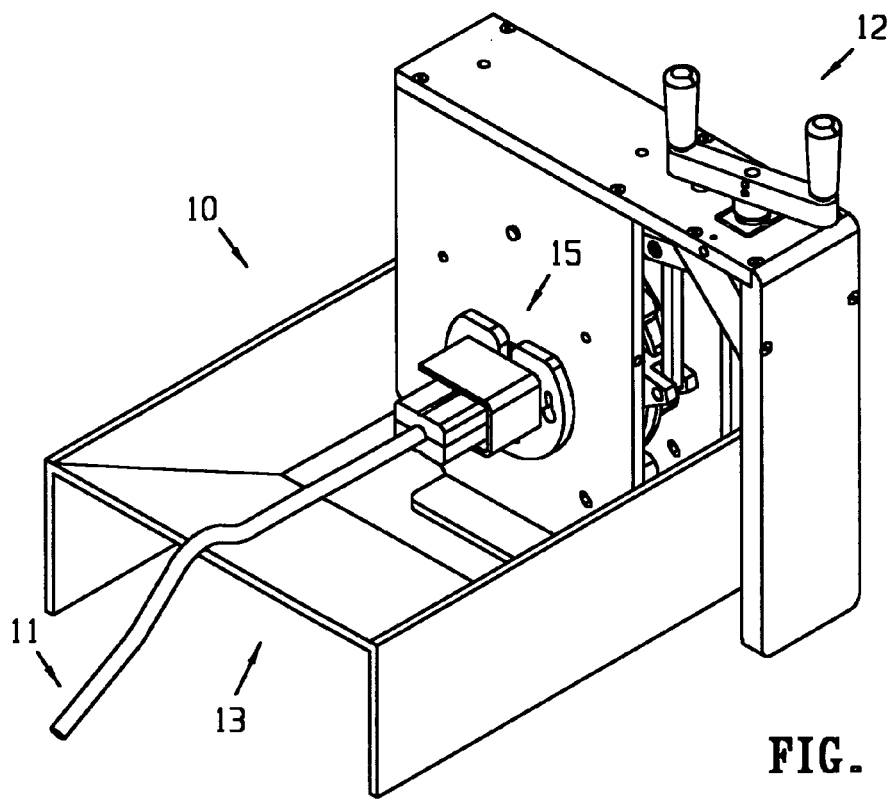
FIG. 2 is a further perspective view of the apparatus.
Figure 3:
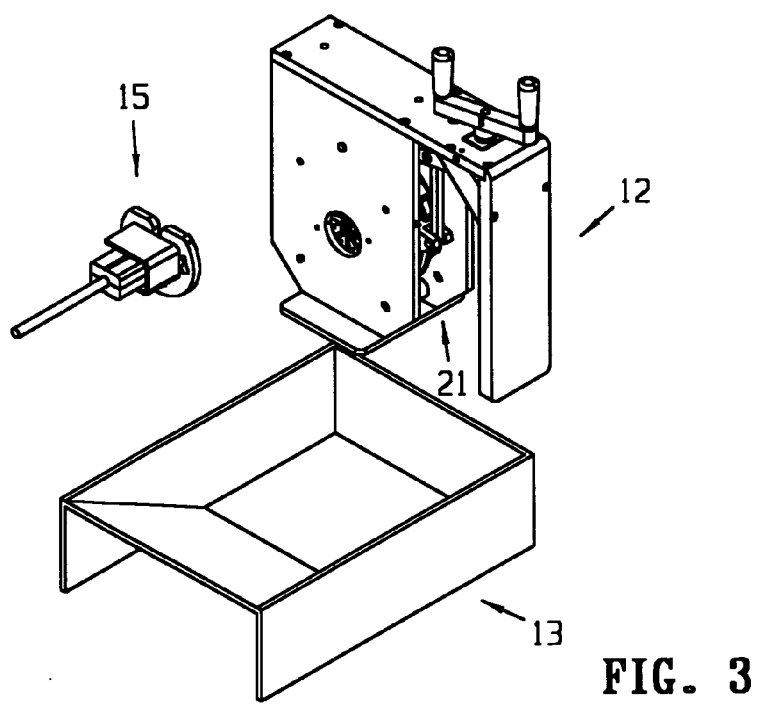
FIG. 3 illustrates embodiments of the tub, catheter clamp and crimping assemblies of the apparatus.

Referring first to FIGS. 1-3, the tissue prosthesis crimping apparatus 10 for loading a prosthesis or other medical device (not shown) into a catheter or sheath 11, or other tubular structure comprises, in general, a crimping assembly 12, a submersion tank or tub 13 for holding a medical solution 14 such as saline, and catheter clamp 15. The apparatus 10 operates while partially submerged in the saline solution 14 which is contained in the removable tub 13. Tank 13 is preferably about 13×7.5 inches, with a height of about 5.25 inches, a maximum liquid volume of about 5.15 liters and a filled weight of about 15 lbs. Only a single person is required to perform all operations of the apparatus. A base or frame portion 19 of the crimping assembly and the catheter clamp 15 are reusable and can be steam and EtO sterilized. All parts in direct contact with the stent or prosthesis, including the crimping elements or segments (described below) of a crimp head or assembly 20, are one-use disposable pieces that are easily interchanged between procedures.

In general, operation of the system 10 first involves placing new crimp elements or segments into the crimp head 20 (preferably with the assistance of a loader), and moving it to a full open position. Next, the machine base 19, including the head 20, is placed into the tub 13. The catheter 11 is secured to the quick release clamp 15. The clamp 15 is secured to the base 19. Next, a prosthesis mated with a stent is inserted into the head 20 for example by hand, and the head 20 is actuated, which closes a central aperture thereof, until the individual crimp elements rest against hard stops. This radially compresses or crimps the stent/prosthesis. The crimped device is pushed (for example via a quill) or pulled (via a device internal to the catheter) into the catheter 11. This apparatus is useable with both balloon expandable and self expanding prosthesis stents. The catheter clamp 15 is removed from the base 19. Finally, the catheter 11 is removed from the clamp 15 with the crimped prosthetic device, for example a heat valve, installed therein.

Figure 6:
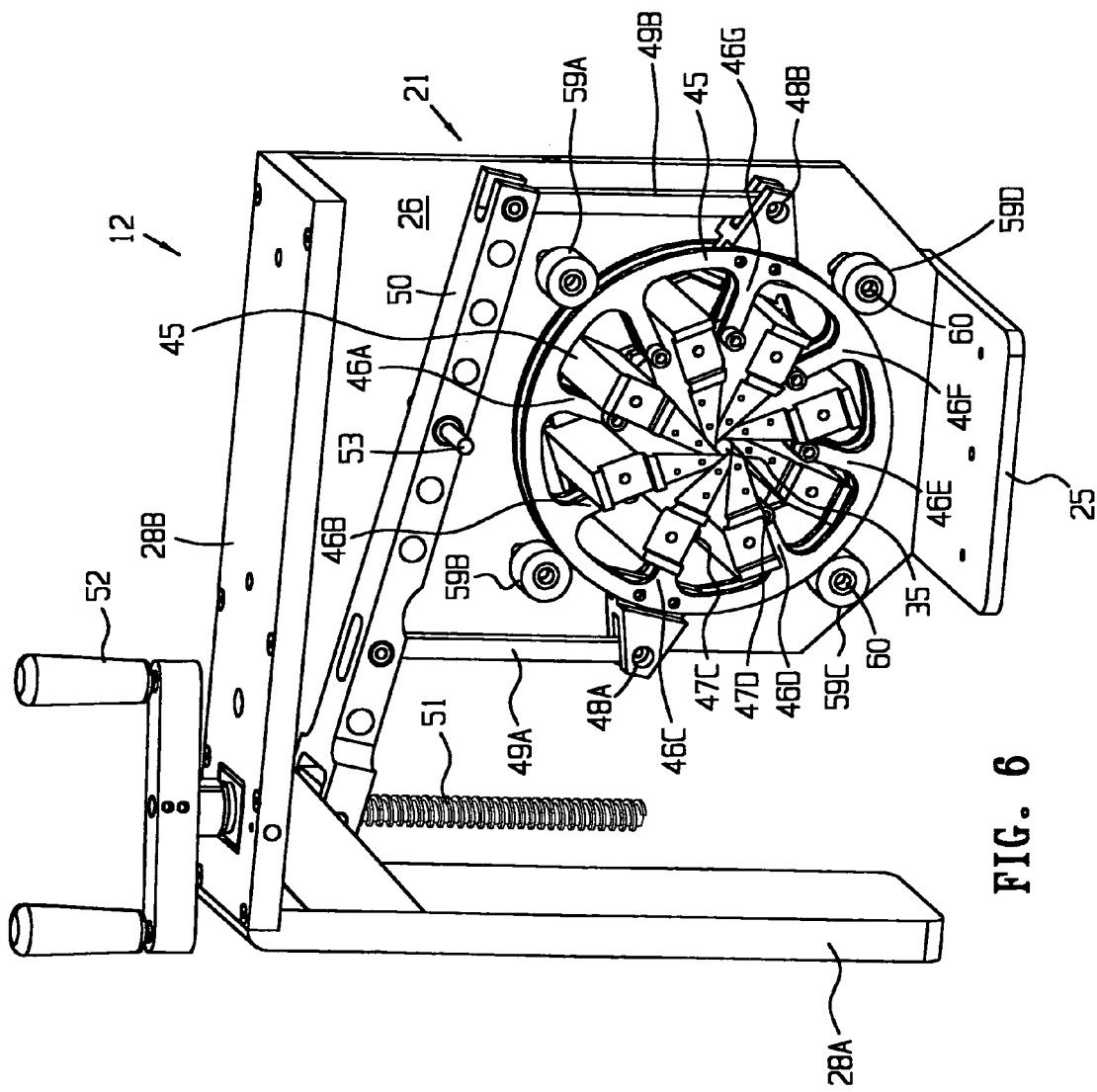
FIG. 6 is a perspective view of the crimping assembly showing an embodiment of the activation ring.

Referring also to FIGS. 4-6, the crimping assembly 12 comprises the base or frame 19, the crimp head 20, and an actuation mechanism 21 connected to the frame and connectable to the crimp head 20. The apparatus also preferably includes an attachable loader 22 for aligning and loading the elements of the crimp head 20 onto actuation mechanism 21.

Figure 8:
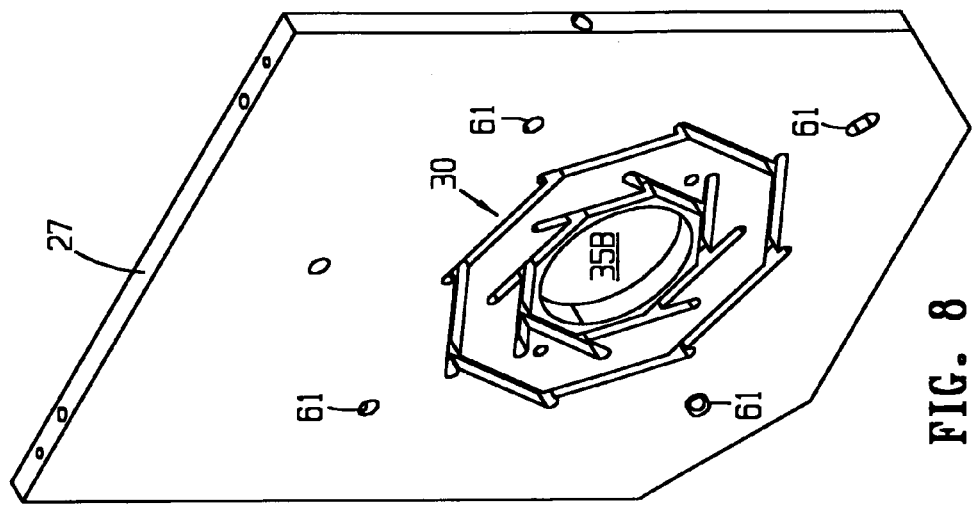
FIG. 8 is a perspective view of the back side of an embodiment of the main face plate of the crimping assembly.
Figure 7:
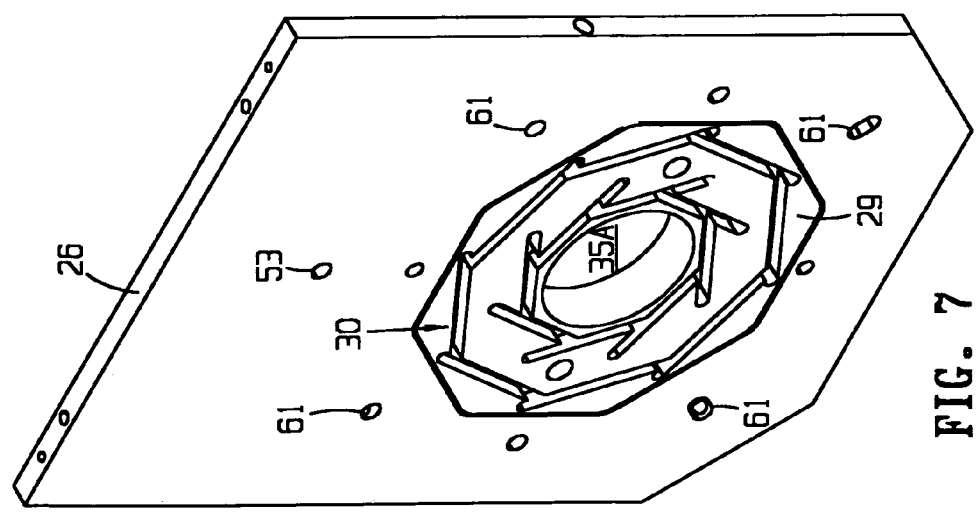
FIG. 7 is a perspective view of the back side of an embodiment of the stationary plate of the crimping assembly.
Figure 9:
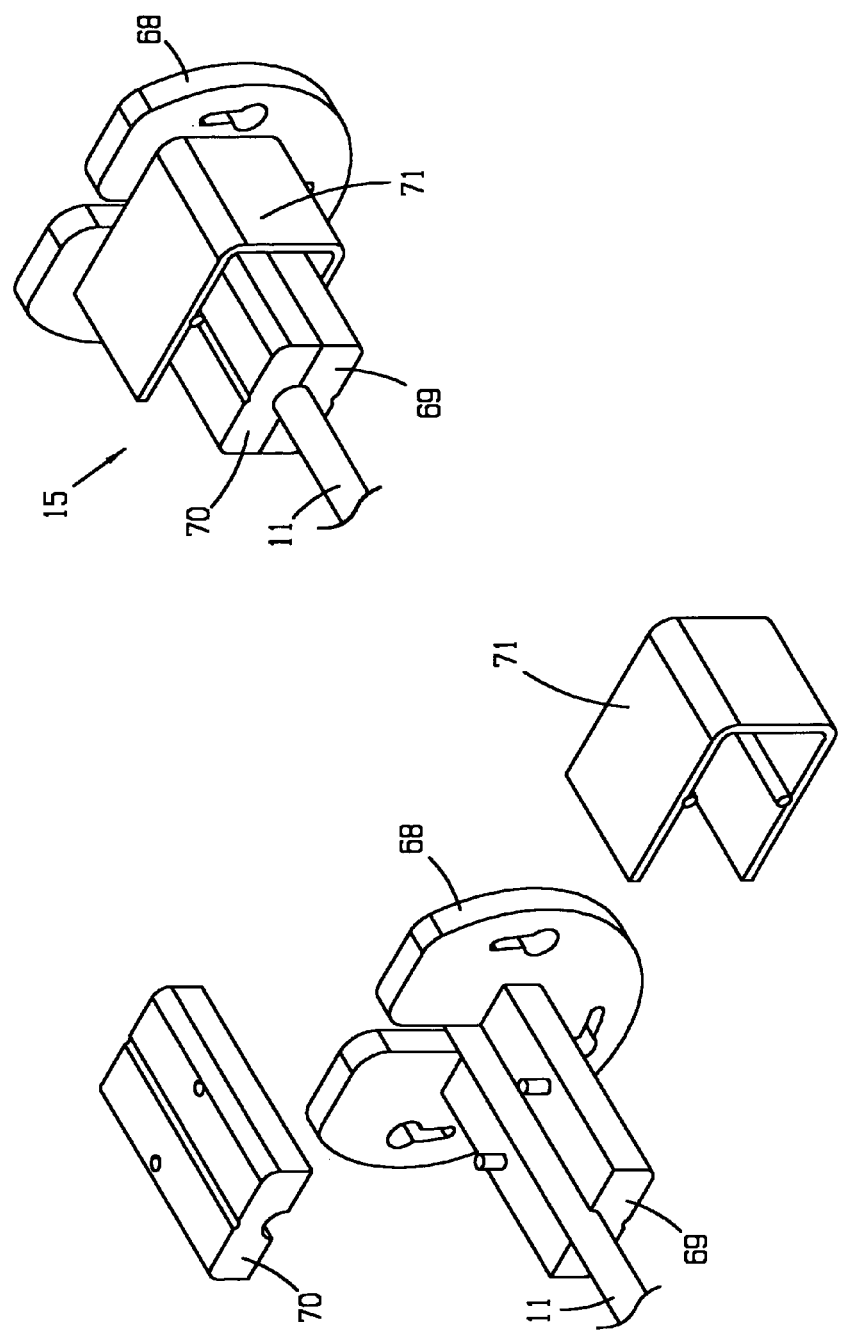
FIG. 9 is an exploded view of an embodiment of the quick change catheter clamp of the apparatus.
Figure 10:
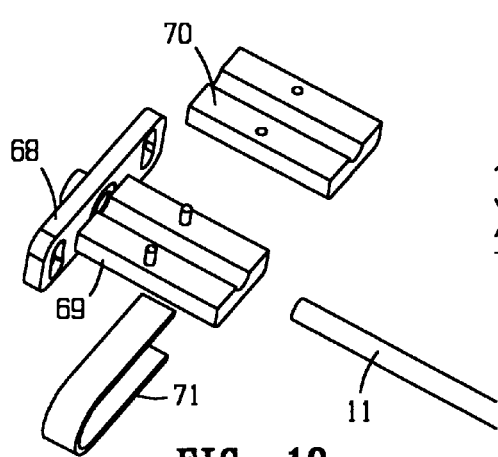
FIGS. 10-15 illustrate a process of using the quick change catheter clamp.
Figure 11:
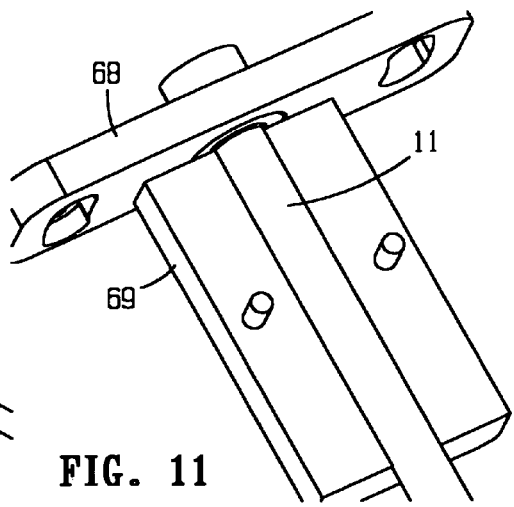
Figure 12:
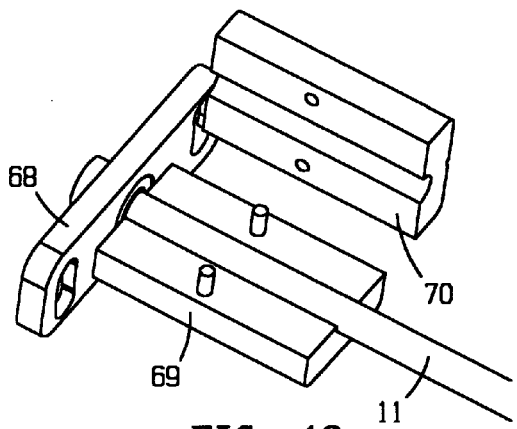
Figure 13:
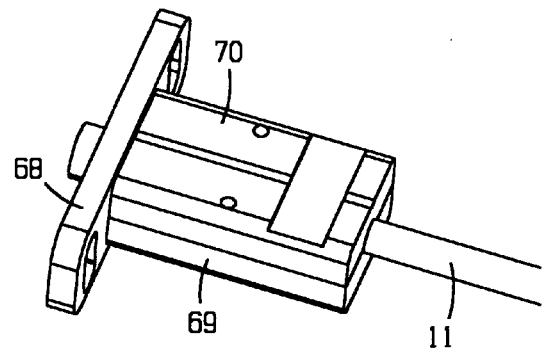
Figure 14:
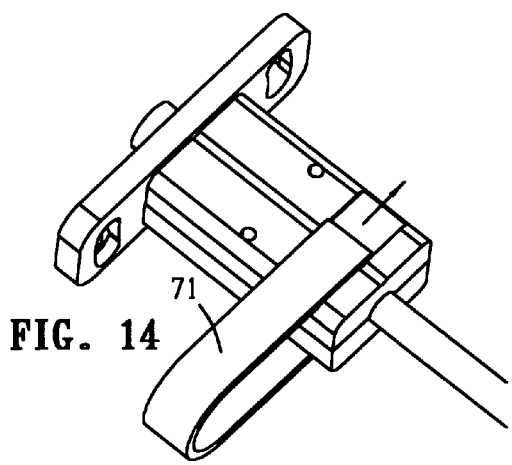
Figure 15:
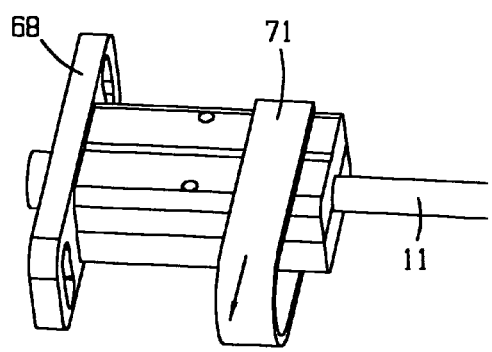
Figure 16:
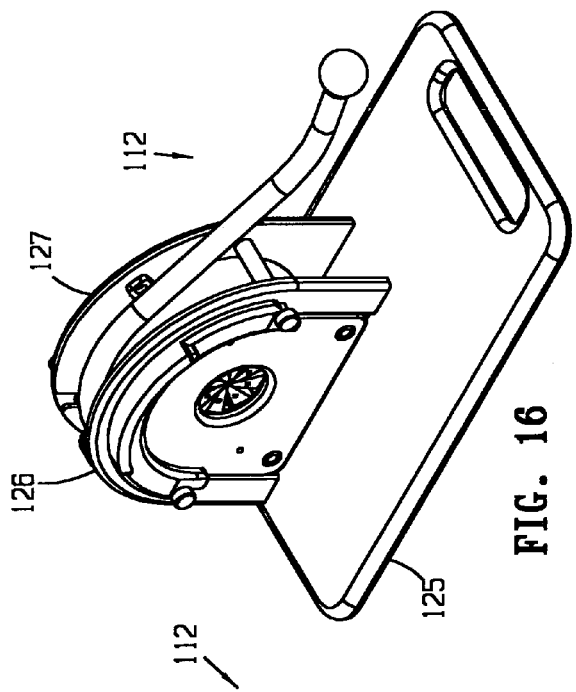
FIG. 16 is a perspective view of an alternative embodiment of the crimping assembly of the apparatus.
Figure 19:
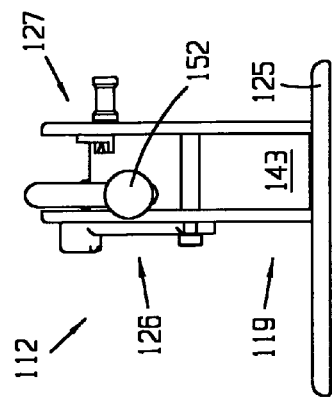
FIG. 19 is an end view thereof.
Figure 18:
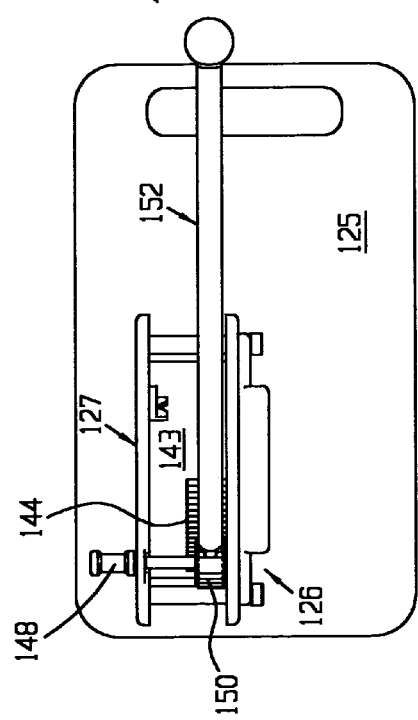
FIG. 18 is a top plan view thereof.
Figure 17:
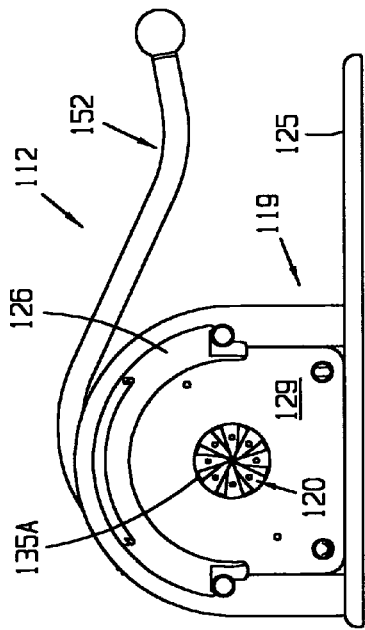
FIG. 17 is a front elevation view of the crimping assembly of FIG. 16.

Referring also to FIGS. 7 and 8, the frame 19 comprises a base member 25, a pair of crimp head retaining members comprising a front plate 26 and a rear plate 27, and side members 28a and b. The base member 25 provides bottom support for the remaining elements of the frame 19. The front and rear plates 26 and 27 extend upwardly from the base member 25 and are separated a predetermined distance. Front plate 26 has a removable face plate 29. Face plate 29 and rear plate 26 each have a predetermined arrangement of linear, angled slide grooves or slots 30 disposed on their inwardly facing surfaces, surrounding coaxial central apertures 35a and b. Each groove configuration 30 preferably have a pair of concentric members which cooperate with slide members on the head 20 elements to provide linear, radial movement to compress the stent/prosthesis, as described later.

Figure 26:
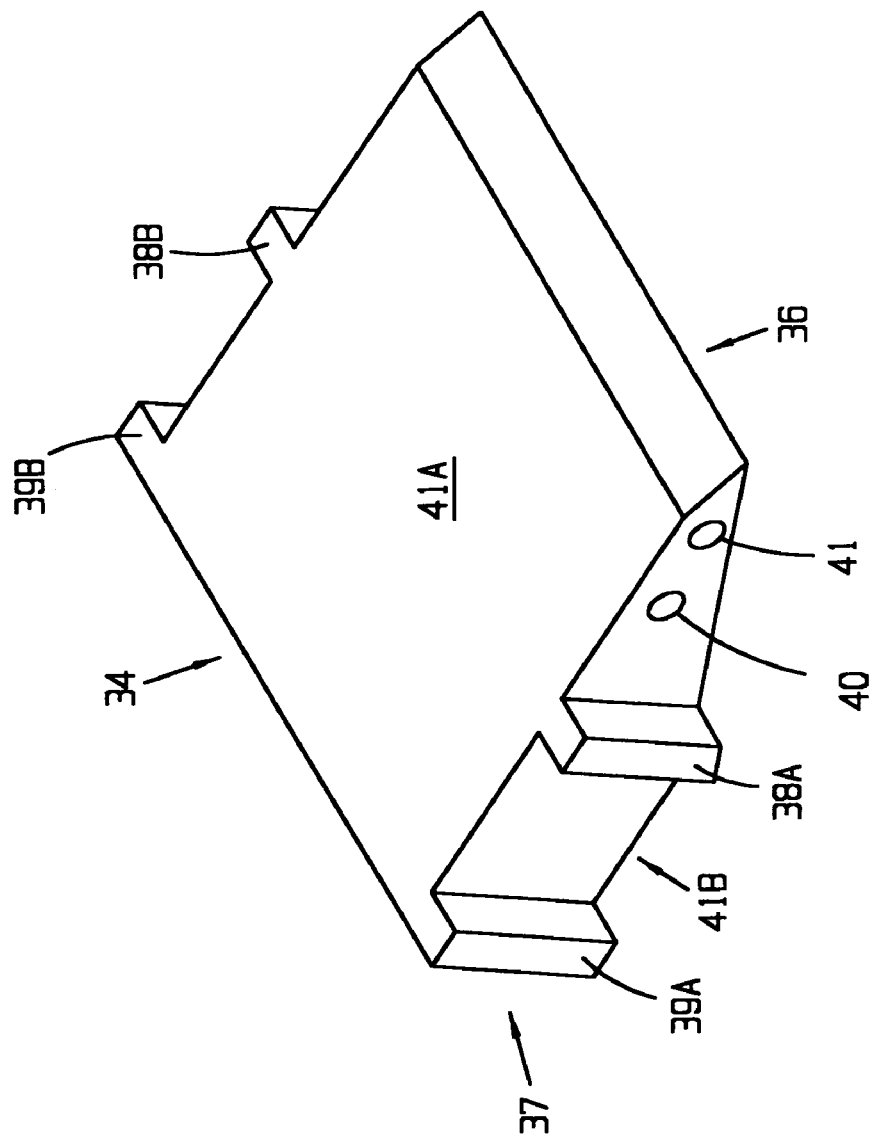
FIG. 26 is a perspective view of an embodiment of a crimping element or segment of the crimping head shown in FIGS. 4 and 6.

Referring also to FIG. 26 the crimp head 20 comprises a plurality, for example eight (8) crimp segments or elements 34a-h which are arranged about and define a central aperture 35. Each segment 34 has a predetermined configuration with an inwardly oriented tapered distal end 36 which is disposed toward the aperture 35 and an outwardly oriented proximal end 37. A pair of distal rectilinear slide blocks or shoulders 38a and b are disposed on the longitudinally oriented (with respect to the working or input/output axis of the apparatus 10 in general) ends of the segment 34. A pair of proximal slide blocks 39a and b are disposed proximally. The slide blocks 38 and 39 mate with slide grooves 30 of the plates 26 and 27. Preferably, at least one loader mating aperture is disposed at each longitudinal end for connection to a loader (not shown). The elements 34 have predetermined substantially flat lateral faces 41a and b which cooperate with the actuator 21, the slide blocks 39 and the slide grooves 30 to move the elements 34. The distal ends are preferably about 50 mm in length.

As is best shown in FIG. 6, the actuator 21 comprises activation ring 43, rollers 47, arms 49, beam 50 and screw 51. A handle 52 is connected to the screw 51 for hand turning by the operator. The screw 51 threadedly connected to an end of the beam 50, which is pivotally connected at pin/aperture 53 to the plates 26 and 27. Arms 49a and b are pivotally connected to the beam 50 at one end and to the ring 43 at the other end, via brackets 48a and b. Ring 43 is preferably bifurcated, but may have a unitary structure. Ring 43 has a circumferential ring portion 45 and a plurality radial spokes 46a-g aligned between the crimp elements 34. Rollers 47a-h are connected to spokes 46. Rotation of the screw 51 moves the beam 50, which moves the arms 49 and causes them to rotate the activation ring 43. This causes rollers 47 to contact and move along the lateral faces 41 of the segments 34. The rotary force of the rollers 47 causes the segments 34 to linearly slide along a predetermined path determined by grooves 30 as a result of slide blocks 39. The distal ends 36 of the segments move toward one another whereby the aperture 35 becomes smaller and closes. The ends 36 engage and radially compress the prosthetic device disposed in the aperture 35.

The preferred maximum opening diameter of the crimp head 20 aperture 35 is about 35 mm and it can close to substantially zero mm. Utilizing the teachings of this invention, the maximum crimping force of the apparatus 10 is about 100 lbs. between two opposing elements 34. Maximum crimping cycles is about 10 per head 20.

Referring to FIGS. 9-15, the catheter clamp 15 comprises a front plate 68 connected to a bottom block 69, a top block 70 and a spring clamp 71. A catheter 11 is placed in a central groove or channel of the bottom block 69 so that its open terminal or distal end abuts the front plate 68. As is known in the art, the catheter 11 has a hollow lumen. Top block 70 is placed over the bottom block so that its groove is aligned with the catheter 11. Clamp 71 is placed over the mated blocks 69 and 70 to hold them in place. Front plate 68 is connectable to the crimping assembly 12 so that the radially compressed, reduced diameter prosthesis can be pushed or pulled into the catheter 11 lumen via its open end. The clamp 15 will accommodate sheaths 11 up to about 8 mm in diameter and about 65 mm in length. Stent diameter reductions of at least 6 mm are obtained.

Operation of the apparatus 10 is relatively simple, which minimizes the need for special operator training. Final close diameter is dependent on the specific crimping elements 34 chosen for a procedure, which substantially minimizes the possibility of operator calibration error. The crank handle 52 requires minimal physical effort to provide adequate crimping force. Introduction of the crimped stent can be accomplished by two means. A hand held quill can be used to manually push the crimped stent out of the base and into the catheter, or the stent may be pulled out of the base and into the catheter by means of an internal catheter device. The catheter clamp set 15 accommodates a wide range of french catheter sizes. The clamps 15 are quickly and easily detached and attached to the apparatus base, which reduces operation cycle time and allows for simple catheter placement. The design of the clamps 15 also provides superior alignment of the stent for insertion into the catheter when compared to other stent introduction means. The insertion aperture of the apparatus 10 minimizes gapping between crimping elements throughout its entire diameter range, which avoids damage to stents during compression. The small size and weight of the apparatus 10 allows for easy storage and transportation.

The modular design of the system 10 also provides several advantages, including disposable element capability, reduced procedure cycle time, reduced storage space requirement, and reduced space requirement for sterilizing procedures. The disposable crimp elements 20 eliminate surface cross-contamination between procedures and allow preset close diameter settings on future machines. The quick-connect catheter clamp 15 allows fast and accurate location of sheath 11 within the clamp 15 and quick attachment/detachment of clamp 15 to the base 12. They also prevent the base 12 from interfering with sheath loading by allowing operators to load the sheath 11 while the clamp 15 is not attached to the base. The C-clamp spring 71 allows quick release and removal of top clamp plate 70 and catheter 11, while doubling as a holding grip. In one embodiment, turn crank 52 and power screw activation provides adequate holding ability at closed position under crimping loads while requiring little effort from the operator. Linearly moving crimping elements 34 reduces gapping between crimping elements 34 during aperture reduction. This also allows for development of zero gapping throughout the entire travel using injection-molded elements 34. Additionally, it permits reduction of the overall size of the machine 10, as well as the disposable elements 34. Quick-change elements 34 or elements set 20 permits easy transportation, sterilization, and loading of the disposable element set 20. It also avoids damage of the crimping elements 24 during shipping and assures correct placement within the machine base 12. The separate submersion tank 13 reduces space required for machine storage, allows the machine to be moved in pieces, and simplifies watertight sealing. An adjustable hard stop embodiment allows fast close diameter adjustment for testing purposes. Polymer plain bearings allow for steam and EtO sterilization while reducing pivot point friction and eliminating corrosion. Lower adjustable bearing axles permit preloading of polymer roller bearings against activation rings.

Referring to FIGS. 16-19, an alternative embodiment of the crimping assembly 112 comprises the base or frame 119, the crimp head 120, and an actuation mechanism 121 connected to the frame 119 and connectable to the crimp head 120. The apparatus also preferably includes an attachable loader 122 for aligning and loading the elements of the crimp head 120 onto actuation mechanism 121.

Figure 20A:
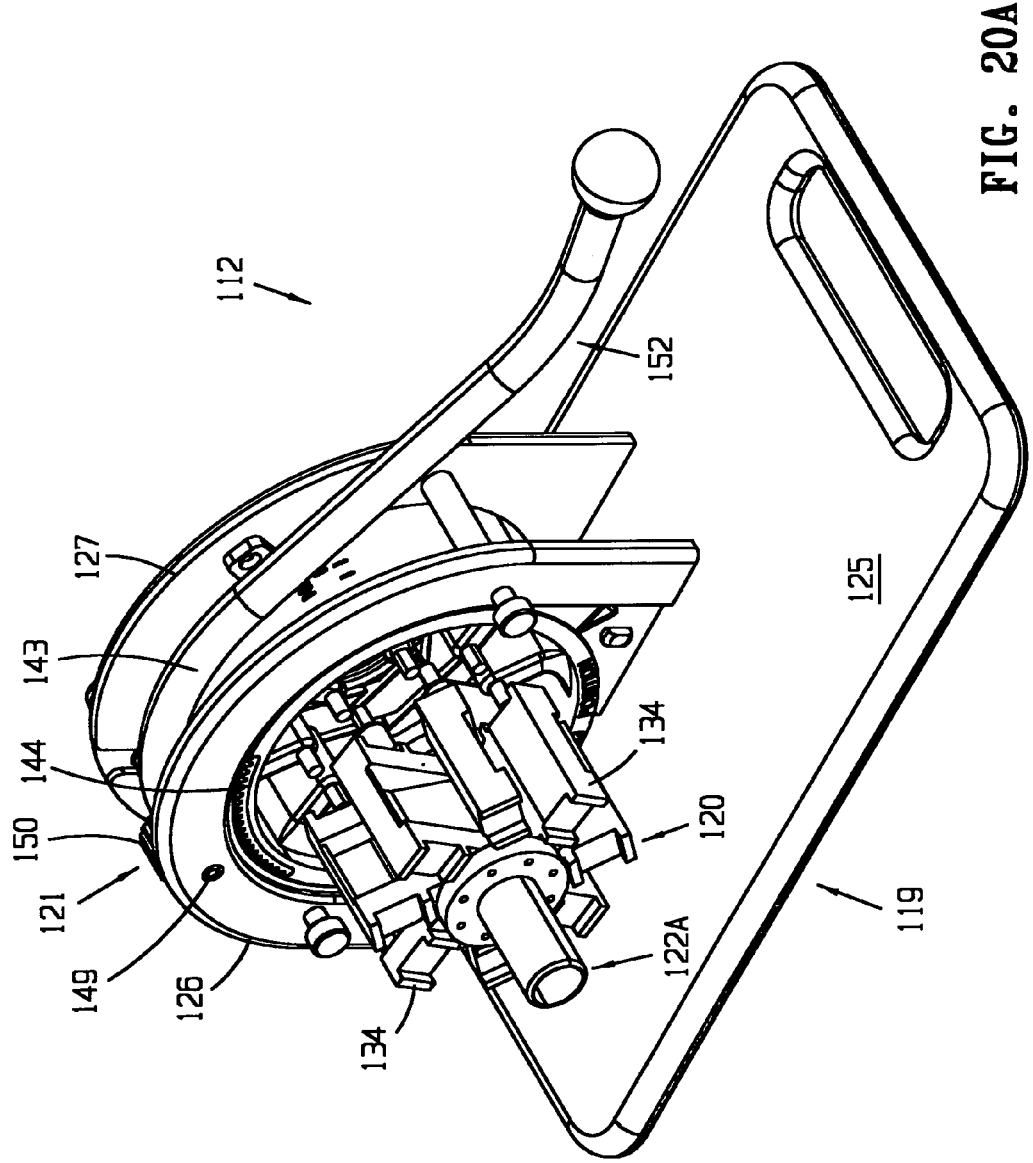
FIG. 20A is another perspective view of the crimping assembly, showing element loading of a fresh set of elements using a loader.
Figure 20B:
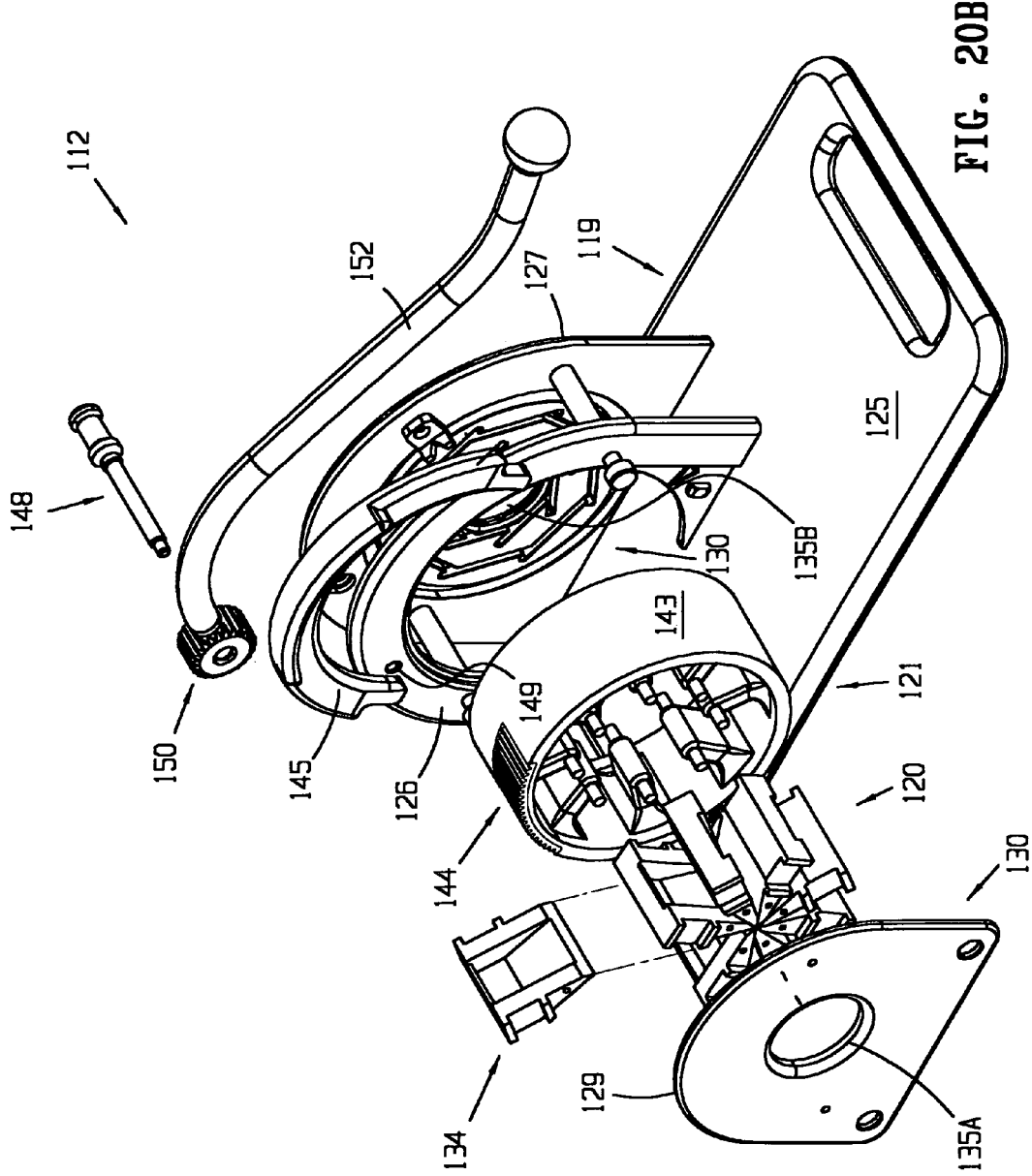
FIG. 20B is an exploded view of the crimping assembly.
Figure 24:
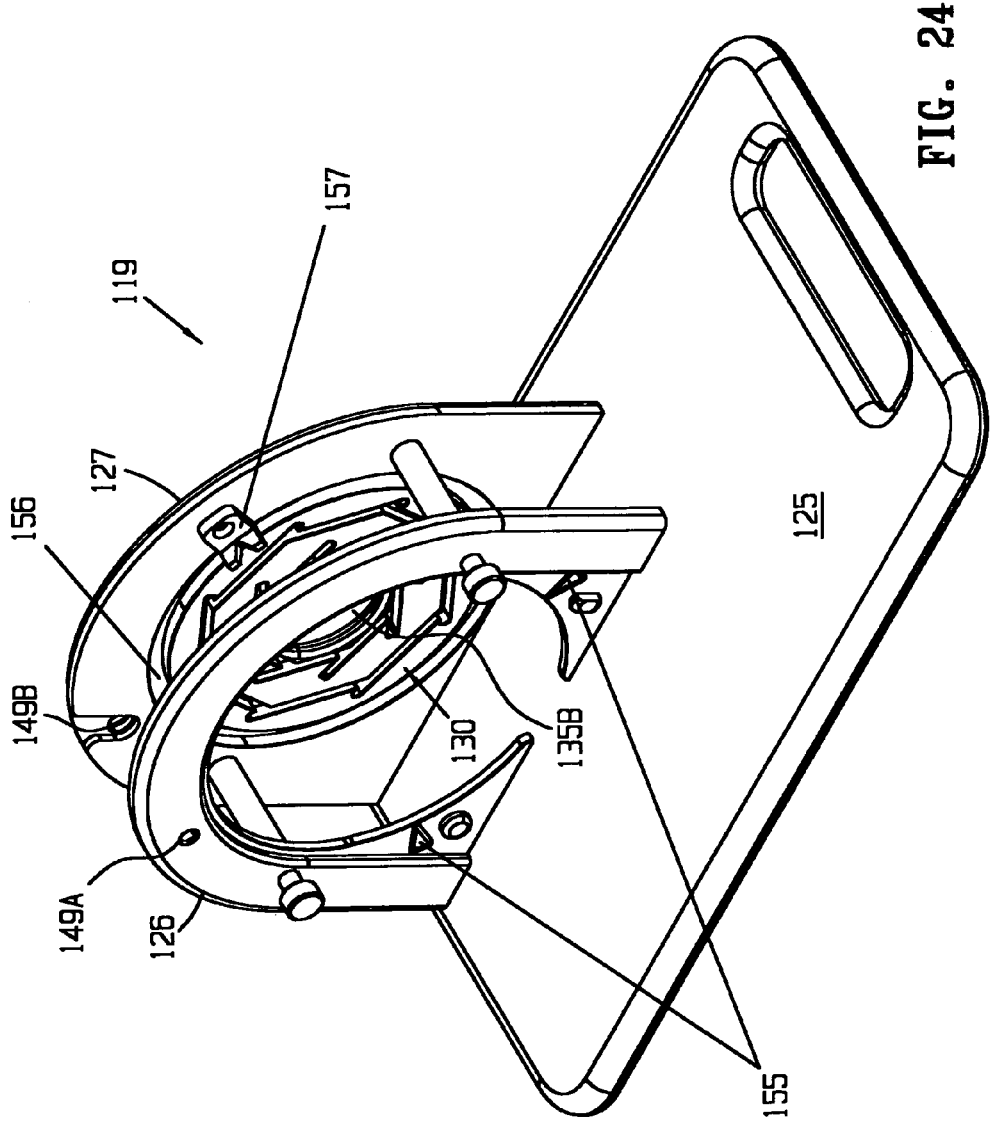
FIG. 24 is a perspective view of embodiments of the base and plates of the crimping assembly.

Referring also to FIGS. 20 and 24, the frame 119 comprises a base member 125, a front frame 126 and a rear frame 127. The base member 125 provides bottom support for the remaining elements of the frame 119. The front and rear plates 126 and 126 extend upwardly from the base member 125 and are separated a predetermined distance. Front plate 126 has a removable face plate 129. Face plate 129 and rear plate 126 each have a predetermined arrangement of linear, angled slide grooves or slots 130 disposed on their inwardly facing surfaces, surrounding coaxial central apertures 135a and b. The groove configuration 130 preferably includes a pair of concentric members which cooperate with slide members on the head 120 elements to provide linear, radial movement to compress the stent/prosthesis.

Figure 25:
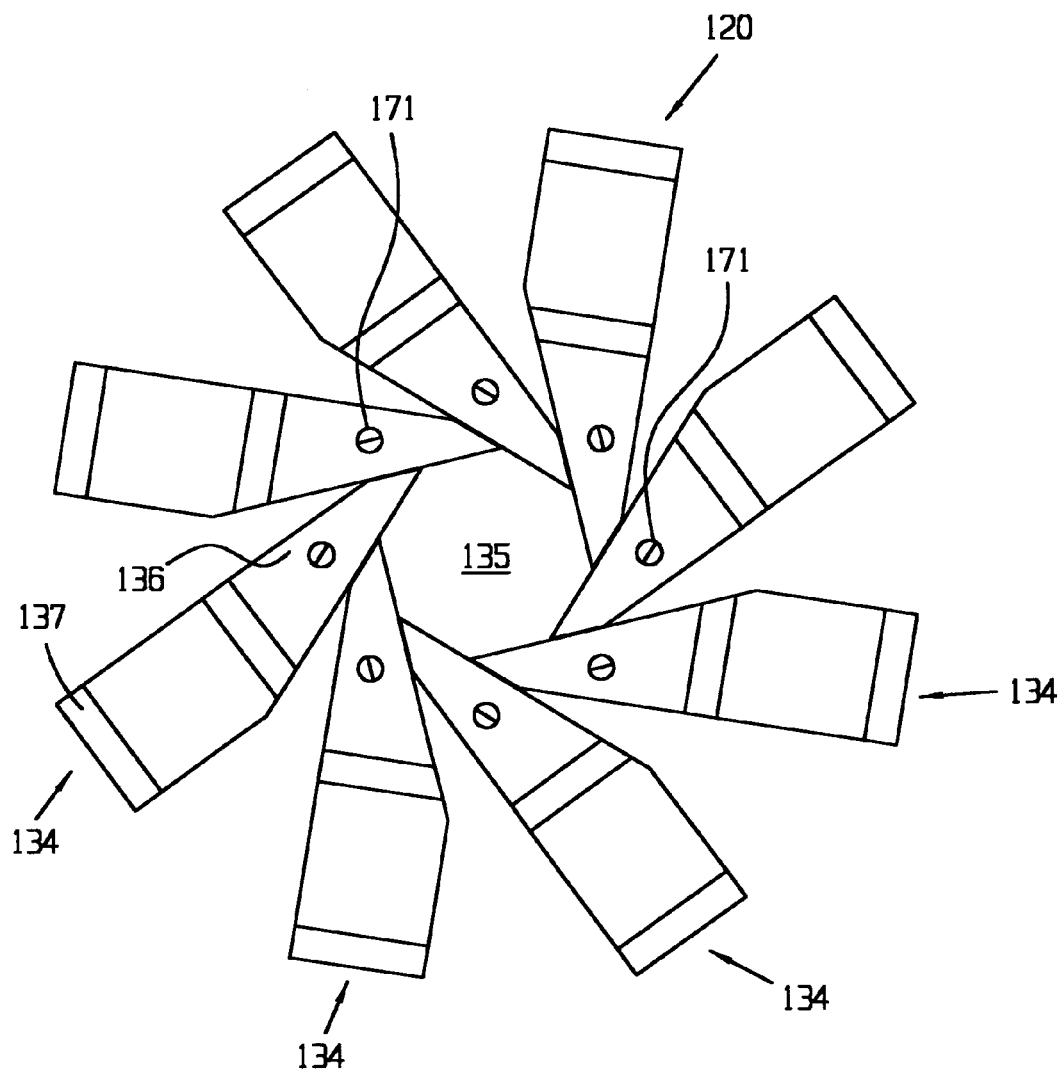
FIG. 25 is a front elevation view of the crimp head.

Referring also to FIGS. 22, 23, and 25 the crimp head 120 comprises a plurality, for example eight (8) crimp segments or elements 134a-h which are arranged about and define a central aperture 135. As is best shown in FIGS. 27-31, each segment 134 has a predetermined configuration with an inwardly oriented tapered distal end 136 which is disposed toward the aperture 135 and an outwardly oriented proximal end 137. A pair of distal rectilinear slide blocks or locating shoulders 138a and b are disposed on the longitudinally oriented (with respect to the working or input/output axis of the apparatus 10 in general) ends of the segment 134. A pair of proximal slide blocks 139a and b are disposed proximally. The slide blocks 138 and 139 mate with slide grooves 130 of the plates 126 and 127. Preferably, at least one loader mating aperture 171 is disposed at each longitudinal end for connection to a loader 122a and b. The elements 134 have predetermined substantially flat lateral faces 141a and b of a predetermined inset configuration on one side, which cooperate with the actuator 121, the slide blocks 139 and the slide grooves 130 to move the elements 134. The distal ends are preferably about 50 mm in length.

Returning to FIGS. 20, 21 and 24 the actuator 121 comprises activation ring 143 with an external gear tooth profile 144 and a plurality of activation pin structures 147 disposed on its interior. The activation ring 143 is held in rotatable place between plates 126 and 127 by a capture plate lock ring 145. A handle 152 is connected to the front plate 126 via a pin 148 at point 149. Handle end has a drive gear 150 which mates with gear tooth profile 144 of activation ring 143. Rotation of the arm 152 moves the gear 150, which moves the activation ring 143. This causes pins 147 to contact and move along the lateral faces 141 of the segments 134. The rotary force of the pins 147 causes the segments 134 to linearly slide along a predetermined path determined by grooves 130 as a result of slide blocks 139. The distal ends 136 of the segments move toward one another whereby the aperture 135 becomes smaller and closes. The ends 136 engage and radially compress the prosthetic device disposed in the aperture 135.

Base 119 further preferably also has segment load position indicating graphics 155, an activation ring locating slot 156, and a handle load position indicator 157 for ease of head 120 replacement.

The descriptions above and the accompanying drawings should be interpreted in the illustrative and not the limited sense. While the invention has been disclosed in connection with an embodiment or embodiments thereof, it should be understood by those skilled in the art that there may be other embodiments which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A medical prosthesis catheter loading apparatus, comprising:

a. a crimping assembly for reducing the diameter of a prosthesis, the crimping assembly comprises a base, a crimp head connectable to the base, and an actuation mechanism connected to the base and connectable to the crimp head to actuate the crimp head, wherein the base comprises a pair of crimp head retaining members, the retaining members being constructed of a sterilizable material, crimp elements, and having a crimp head element guide with at least two concentric arrangements of linear grooves; and b. a catheter clamp for holding a catheter adjacent to the prosthesis.

2. The apparatus of claim 1, wherein the crimp head comprises a plurality of crimp elements arranged about a central crimp aperture.

3. The apparatus of claim 2, wherein the elements linearly move to vary the size of the central crimp aperture.

4. The apparatus of claim 2, wherein each crimp element has a distal end disposed near the central aperture and a proximal end disposed away from the central aperture, each element further having a distal rectilinear slide block, a proximal rectilinear slide block, and at least one flat actuation surface.

5. The apparatus of claim 2, wherein the head is readily disposable.

6. The apparatus of claim 5, further comprising an element loader for configuring the crimp elements.

7. The apparatus of claim 2, wherein the actuation mechanism comprises a rotatable activation ring communicatively connected to the crimp elements to move them linearly toward the central crimp aperture.

8. The apparatus of claim 7, wherein the activation ring is communicatively connected to the crimp elements via element contacting rollers.

9. The apparatus of claim 7, wherein the activation ring is communicatively connected to the crimp elements via element contacting pins.

10. The apparatus of claim 7, wherein the actuation mechanism further comprises a screw connected to the activation ring via a lever arrangement.

11. The apparatus of claim 7, wherein the actuation mechanism further comprises an arm connected to the activation ring via a gear arrangement.

12. The apparatus of claim 1, wherein the catheter clamp comprises a pair of blocks, each having slot for engaging a portion of a catheter, and a clamp for holding the blocks together, the blocks and clamp being constructed of a sterilizable material.

13. The apparatus of claim 12, wherein at least one block has a face for connecting to the crimping assembly.

14. The apparatus of claim 1, further comprising a submersion tank for holding a predetermined amount of a medical solution and adapted for enclosing at least a portion of the crimping assembly and the catheter clamp.

* * * * *